United States Patent
Stoltz

(10) Patent No.: US 6,827,948 B2
(45) Date of Patent: Dec. 7, 2004

(54) METHOD AND COMPOSITIONS FOR PROCESSING POULTRY FEATHERS

(75) Inventor: Michael J. Stoltz, Duncansville, PA (US)

(73) Assignee: Steen Research LLC, West Linn, OR (US)

( * ) Notice: Subject to any disclaimer, the term of this patent is extended or adjusted under 35 U.S.C. 154(b) by 165 days.

(21) Appl. No.: 10/278,477

(22) Filed: Oct. 22, 2002

(65) Prior Publication Data

US 2003/0075289 A1 Apr. 24, 2003

Related U.S. Application Data

(60) Provisional application No. 60/346,046, filed on Oct. 23, 2001.

(51) Int. Cl.[7] ........................... A61K 35/24; C14M 1/00; D06M 17/00; C07K 1/00; C07K 17/00
(52) U.S. Cl. ........................... 424/543; 8/94.1; 530/355; 530/357; 530/412
(58) Field of Search ........................... 424/543; 8/94.1; 530/355, 357, 412

(56) References Cited

U.S. PATENT DOCUMENTS

| 2,857,237 A | * 10/1958 | Frederick et al. ........... 8/94.1 R |
| 3,475,112 A | * 10/1969 | Mahall ....................... 8/94.1 R |
| 4,151,306 A | 4/1979 | Williams et al. |
| 4,169,706 A | 10/1979 | Kruchen |
| 4,869,829 A | 9/1989 | Casey |
| 5,616,150 A | 4/1997 | Moeller et al. |
| 5,705,030 A | 1/1998 | Gassner, III et al. |
| 6,027,608 A | 2/2000 | Gassner |
| 6,238,486 B1 | 5/2001 | Dunham et al. |

FOREIGN PATENT DOCUMENTS

| JP | 55026226 | 2/1980 |
| JP | 55030404 | 3/1980 |

* cited by examiner

*Primary Examiner*—Christopher R. Tate
(74) *Attorney, Agent, or Firm*—Morgan, Lewis & Bockius LLP

(57) ABSTRACT

The present invention provides a method and compositions for processing poultry feathers. In one embodiment, the method for processing poultry feathers comprises contacting a plurality of poultry feathers having an average particle size with a detergent capable of imparting a static charge to the plurality of poultry feathers; reducing the average particle size of the plurality of poultry feathers; increasing entanglement of the plurality of poultry feathers; adding an anionic polymeric adduct to the plurality of poultry feathers; adding a cationic species to the plurality of poultry feathers; and dewatering the plurality of poultry feathers. In another embodiment, a composition for processing poultry feathers, comprises a detergent capable removing at least a portion of fats and oils from a poultry feather and imparting a static charge to the poultry feather; an antimicrobial compound; an anionic polymeric adduct; and a cationic species.

27 Claims, 1 Drawing Sheet

METHOD AND COMPOSITIONS FOR PROCESSING POULTRY FEATHERS

This application claims the benefit of U.S. Provisional Application No. 60/346,046 filed on Oct. 23, 2001, which is incorporated by reference herein in its entirety.

BACKGROUND OF THE INVENTION

1. Field of the Invention

The invention relates generally to a method and compositions for processing poultry feathers. More specifically, the invention is directed to a method and chemical compositions for cleaning and preparing poultry feathers for further processing into usable items.

2. Description of Related Art

Poultry slaughtering creates a significant amount of by-products including, for example, offal and feathers. Such byproducts made be disposed of through burning or burial. Alternatively, the feathers may be hydrolyzed and dried into meal and reintroduced into the food chain due to the high usable protein content of the feathers. The feathers may also be further processed into predetermined shapes or for subsequent use in the construction of other usable products. For example, the feathers may be processed into fibers that are incorporated into the structure of other products such as paper, filters, wovens and non-wovens, extrusions, laminates and composites, fillers, insulation, packing, adsorbents, biodegradable horticultural pots, mats, and other matrix-like products. In these cases, the feathers are typically washed to remove fats and oils and subsequently dried.

In processing poultry feathers, it is desirable to process the feathers in a manner that provides the feathers or feather mass with good dewatering properties so that, for example, any washing solutions may be easily drained. Further it is desirable to process the feathers so that they have sufficient structural integrity for subsequent use, particularly when the feathers are intended for further processing into predetermined shapes or for use in the construction of certain products.

Current feather washing processes are equipment-intensive and, therefore, capital-intensive. For example, some feather washing processes use solvents, such as chlorinated hydrocarbons, that require solvent washers and distillation and recycling equipment. Other processes use ethanol, ketones, or esters as cleaners, which also require distillation and recycling equipment. Further, some of these solvents are flammable and introduce a significant health and safety risk to personnel utilizing them.

Based on the foregoing, there is a need for a method for processing poultry feathers with minimal capital investment as well as simplicity in use. Further, there is a need for a method for processing poultry feathers that imparts desirable properties to the feather material, such as improved dewatering properties and structural integrity, to enhance the usability of the feather material for other purposes.

SUMMARY OF THE INVENTION

Accordingly, the present invention provides a method and compositions for processing poultry feathers. In one embodiment, the present invention provides a method for processing poultry feathers, comprising contacting a plurality of poultry feathers with a detergent capable of imparting a static charge to the plurality of poultry feathers; adding an anionic polymeric adduct to the plurality of poultry feathers; adding a cationic species to the plurality of poultry feathers; and dewatering the plurality of poultry feathers.

In another embodiment, the present invention provides a composition for processing poultry feathers, comprising a detergent capable of imparting a static charge to the poultry feather; an anionic polymeric adduct; and a cationic species. Such compositions may generally comprise surfactant-based cleaners, static additives, and polymeric substrates.

The present invention provides a method and compositions for processing poultry feathers in a low capital-intensive manner since the method can be practiced using relatively simple processing equipment. Further, the method utilizes chemicals and chemical compositions that are environmentally safe and, therefore, relatively safe to use compared to the chemicals used in other poultry cleaning processes. The method and compositions of the present invention also impart desirable properties to the feathers or feather mass, such as improved dewatering properties and structural integrity, to enhance the usability of the feathers for other purposes, such as in the construction of other usable products.

These and other features and benefits of the present invention will appear from the following description from which the preferred embodiments are set forth in detail in conjunction with the accompanying drawing.

DETAILED DESCRIPTION OF THE PREFERRED EMBODIMENTS

Figure 1:
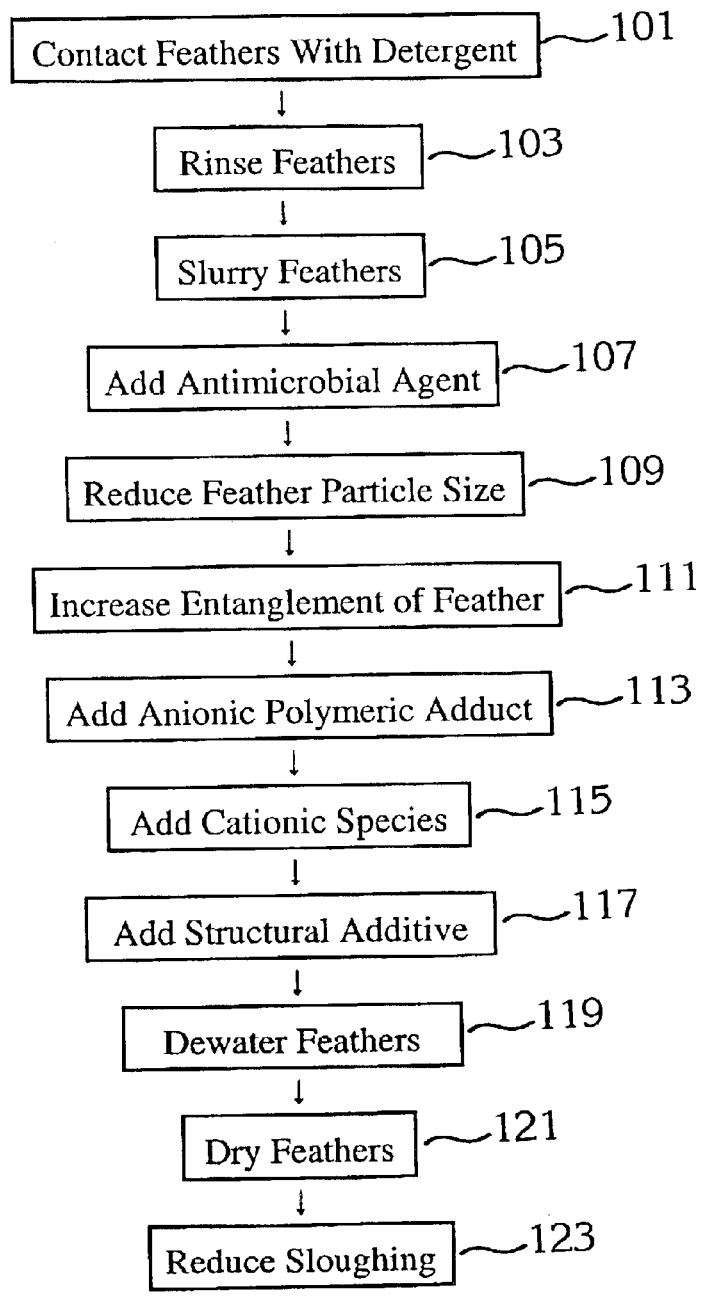
FIG. 1 is a flow schematic of a method for processing poultry feathers according to one embodiment of the present invention.

Generally, the present invention is directed to a method of processing poultry feathers. More specifically, in one embodiment, the present invention is directed to a method for processing poultry feathers, such as chicken feathers, using certain chemicals and chemical compositions that are capable of cleaning the feathers and imparting to the feathers certain desirable properties, including, for example, dewatering properties and structural integrity. Dewatering properties need to be sufficient to allow the feathers or feather mass being processed to pass liquid in an acceptable manner and within an acceptable time. As will be discussed below, sufficient dewatering properties allow any cleaning solutions, rinses, or other chemicals to be drained from the feathers or feather mass in an acceptable manner and time. Structural integrity of the feathers or feather mass is important, particularly in the case where the feathers will be further processed for use in the construction of other usable products, referred to as secondary processing. For example, such secondary processing may require transportation of the feathers or feather mass to another location. In this case, having a feather mass with sufficient structural integrity or cohesiveness makes handling and transportation easier. Further, the structural integrity of the feathers or feather mass in the construction of other usable products is obviously important since the feathers or feather mass will be integral to the structure and rigidity of the form or shape of such products.

Imparting desirable dewatering properties and structural integrity to the feathers or feather mass can be accomplished in several ways. One method is by utilizing a chemical or chemical composition that imparts a static charge to the feathers. Such a static charge provides a chemical static bond or intermolecular bond between the feathers that allows them to become or remain cohesive. Cohesiveness of the feathers allows them to be more easily dewatered and provides structural integrity to the feathers or feather mass. A static charge may be imparted to the feathers through the use of certain chemicals or chemical compositions according to the present invention. Another method for imparting structural integrity to the feathers or feather mass is by utilizing a polymer additive according to the present invention. Both of these are described in more detail below. It should be appreciated that increasing the cohesiveness of the feathers also reduces sloughing of feather dust or particulate matter from a product made using the processed feathers.

FIG. 1 is a flow schematic of a method for processing poultry feathers according to one embodiment of the present invention. In the step 101, a plurality of feathers, which may be referred to as a feather mass, from a poultry plucking operation or similar operation are contacted with a detergent. It should be appreciated that while the present invention is described in terms of poultry feathers, for example, chicken feathers, it is applicable to feathers from any particular species. The contacting may be accomplished by any method known in the art. Preferably, the contacting is a washing step in which the detergent is combined with water and mixed with the feather mass, wherein such solution is referred to as a washing solution. The contacting may be performed in any mixing device, such as an agitated tank, capable of holding the feather mass and the detergent and capable of providing sufficient contact between the feather mass and the detergent. In this case, the feathers may be simply added to the tank, which is then filled with water, or visa versa. The detergent may be added before, during, or after the addition of the feathers and water to the tank.

The detergent may be a single chemical compound or a mixture of chemical compounds, which is referred to as a chemical composition. Preferably the detergent is any chemical compound or mixture that is capable of at least partially removing fats or oils from the feathers without significantly degrading the feather structure. Such a detergent is similar to commercially available shampoos. Preferably, the detergent is a chemical compound or mixture that is capable of also imparting at least some static charge to the feathers. Most preferably, the detergent is a chemical compound or mixture that is capable of at least partially removing fats and oils from the feathers without significantly degrading the structure of the feathers and is capable of leaving a slight deposition on the feathers, even after rinsing, which imparts a static charge on the feathers. Preferably, the detergent is a chemical compound or mixture that provides sufficient speed in wetting the feathers and in solvency of the fats and oils on the feathers.

The detergent may include any of the following chemicals: alkyl amine oxides, ethyleneoxide, propylene oxide adducts of alcohols, phosphate esters, ethyeneoxide/propylene oxide block copolymers, alkyl ethers, alkyl ether sulfates, alkoxylated alkyphenols, fatty or fatty amine betaines, ethylene oxide/propylene oxide adducts of fatty acids, glycosides, alkyl benzene sulfonic acids, alkyl benzene sulfonates, olefin sulfonates, neutralized fatty acid amides, alcohol sulfates, neutralized salts of alcohol sulfates, fatty acid alkanolamides, polyethylene glycol esters of fatty carboxylic acids, glycol ethers, butyl solvents, sodium silicate, metasilicate, phosphates and alkanolamines. It should be appreciated that the detergent may be any combination of the foregoing chemicals as well.

Particularly preferred detergents include the following chemicals: ethoxylated/propoxylated alcohol with a hydrophobic lipophilic balance of 8.5–30, phosphoric acid ester, ethylene oxide/propylene oxide block copolymer with a hydrophobic lipophilic balance of 8.5–20, alkyl ether sulfate, alkoyxlated alkylphenol, fatty or fatty amino betaine, ethoxylated/propoxylated fatty acid, gylcosides, alkyl benzene sulfonic acid, alkyl benzene sulfonate, olefin sulfonate, neutralized fatty acid amide, alcohol sulfate, sodium or ammonium salt of alcohol sulfate, fatty acid alkanolamide, alkanolamine, sodium metasilicate, sodium silicate, and tridsodium phosphate. It should also be appreciated that the detergent may be any combination of the foregoing chemical compounds as well.

Most preferable combinations include those that provide sufficient wetting of the feathers, high solvency for the fats and oils on the feathers, and the ability to impart an anionic static charge after rinsing. Some preferred combinations include the combination of glycol ether with any of the aforementioned chemicals useful as the detergent. More preferably, the detergent may comprise the combination of glycol ether with any of the following ethoxylated/propoxylated alcohol with a hydrophobic lipophilic balance of 8.5–30, phosphoric acid ester, ethylene oxide/propylene oxide block copolymer with a hydrophobic lipophilic balance of 8.5–20, alkyl ether sulfate, alkoyxlated alkylphenol, fatty or fatty amino betaine, ethoxylated/propoxylated fatty acid, gylcosides, alkyl benzene sulfonic acid, alkyl benzene sulfonate, olefin sulfonate, neutralized fatty acid amide, alcohol sulfate, sodium or ammonium salt of alcohol sulfate, fatty acid alkanolamide, alkanolamine, sodium metasilicate, sodium silicate, and tridsodium phosphate. More preferred combinations include a phophate ester of any of the foregoing chemicals as it is believed that the phosphate ester provides an anionic static charge when placed in contact with the feathers.

The detergent is added in an amount sufficient to reduce the fats and oils contained on the feathers. Preferably, the detergent is selected and used in a concentration sufficient to reduce the content of fats and oils on the feathers to less than 1%, which may be determined by analysis of the remaining fat and oil content of the feathers. Preferably, the detergent is added at a concentration of approximately 300–500 mg/kg of dry feather mass. The specific method of addition of the detergent to the wash solution may include a batch addition or a metered addition. The addition may also be continuous.

The detergent may optionally be combined with a dispersing aid to assist in mixing the detergent with the feathers. Such a dispersing aid is any chemical compound that enhances the dispersion of the selected detergent throughout the washing solution. Such a dispersing aid is preferably a homopolymer, a copolymer, or a terpolymer of acrylic acid. The detergent may also optionally be combined with a solvent such as a butyl solvent; however, it is preferable to not use a solvent unless necessary to aid is the solubility of the detergent in the washing solution.

In the step 103, the feathers or feather mass are rinsed to remove the bulk of the detergent, including any dispersing aid or other solvent from the feather mass. It should be appreciated, however, that such rinsing should not be so aggressive as to remove the deposition on the feathers that imparts the static charge. Rinsing may be accomplished in the same tank used for contacting the detergent with the feathers, for example, by filling the tank with a rinsing solution and agitating the solution and the feathers. The rinsing solution may be water or any other liquid provided such does not remove the deposition on the feathers that provides the static charge. The rinse water or rinsing solution is then drained from the feather mass. It should be appreciated that any method for rinsing and dewatering the rinse solution may be used, such as filtering. It should be appreciated that while desirable, rinsing is not required, in which case, the detergent or washing solution may simply be drained or the feather mass may be separated from the washing solution using, for example, a filter.

Depending upon the final use of the feather mass, it may be possible to stop processing of the feathers at this point and simply use the feather mass after rinsing. For example, where the feather mass is utilized on-site, it may not be necessary to continue processing of the feathers, and the static charge imparted from the detergent may be sufficient. In this case, the feather mass could simply be dried by any method known in the art, such as oven drying, and used as is or in any secondary processing operation.

In the step 105, the feathers are slurried, preferably with water. Again, this may be accomplished using the same tank by simply adding water to the rinsed feather mass. The concentration of the slurry may be up to 10% by weight of dry feathers, but more preferably is approximately 0.5–1% by weight of dry feathers.

In the step 107, an antimicrobial agent may be added to the slurried feathers. It should be appreciated that it is not mandatory for the present invention to add an antimicrobial agent. However, the feather mass must be used very quickly before the onset of microbial or bacterial growth, which may reduce the structural integrity of the feather mass. The antimicrobial compound may be any compound capable of reducing or prohibiting microbial or bacterial growth. Preferably, the antimicrobial compound should not act to degrade the alpha helix keratin structure of the feathers. Exemplary antimicrobial compounds include hydrogen peroxide, gluteraldehyde, and methylene bis-thiocyanate. One of skill in the art will appreciate that the amount of anitmicrobial compound added should be sufficient to minimize any bacterial or microbial growth.

In the step 109, the feathers are processed to reduce their average size. It should be appreciated that the feathers comprising the feather mass each have a particular size. This size is referred to as the particle size or feather size, and a given feather mass has an average particle size. It is desirable to reduce the average particle size of the feathers since they are more easily processed if the average size is smaller. For example, it is easier to agitate, pump, and handle an aggregate mass of feathers having a smaller size. Preferably, reducing the average particle size of the feather mass also results in a feather mass having a more uniform particle size. In other words, the standard deviation associated with the average particle size may be reduced so that the particle size distribution of the feather mass reflects a more uniform particle size or a more narrow particle size range.

The average particle size of the feather mass may be reduced by processing the aqueous feather slurry using any means known in the art that reduces particle size and, preferably, provides for a more uniform size. For example, the slurry may be processed using ball milling, colloid milling, refining, or processes known in cellulose derivative manufacturing.

In the step 111, the entanglement of the feathers in the feather mass is increased. Such entanglement refers to the intertwining of the feather strands amongst themselves in the feather mass. Increasing the entanglement of the feathers is important in imparting structural integrity to the feather mass, which, in turn, also aids in ease of handling and subsequent processing. One manner in which the feathers may be entangled is by fibrillation enhancement of the keratin strand of the feathers.

It should be appreciated that although the entanglement is shown as a separate step, it may be performed concurrently with the processing of the feathers to reduce their average particle size. In other words, the same processing equipment used for reducing the particle size can be used to increase entanglement and such processing may concurrently reduce the average particle size as well as increase entanglement of the feather mass. Therefore, it should be appreciated that preferably, steps 109 and 111 are performed using the same equipment and at the same time. It should also be appreciated that increasing the entanglement of the feathers can be performed without step 109, such that it is not necessary to reduce the particle size of the feathers per se, as long as entanglement of the feathers is accomplished.

In the step 113, an anionic polymer adduct is added to the slurried feathers or feather mass. As noted above, it is desirable to provide structural integrity or cohesiveness to the feather mass for purposes of better handling and use as a structural component in the construction of other products. Since, for example, the feathers lack the fibrils and hydrogen bonding capacity of cellulose, it is desirable to impart a chemical static bonding property to the feathers. This static bond is believed to be an intermolecular bond between the feathers that causes them to remain cohesive as they are further processed and dewatered. While the detergent imparts a static charge to the feathers to provide this cohesiveness, to impart an even greater wet processing bond strength, an anionic polymeric adduct added. Without being limited to any particular theory, it is believed that the anionic polymeric adduct is electrostatically attracted to the amino moiety in the feather structure. The balance of anionic polymeric adduct then entangles the feather mass.

This anionic polymeric adduct may be added by any manner known in the art to the slurried feathers and mixed. In addition, the same tank used throughout may be continued to be used. This anionic polymeric adduct may be any anionic polymer known in the art or any chemical compound capable of imparting an anionic charge to the feathers, which results in entanglement of the feathers in the feather mass. Preferably, the anionic polymeric adduct is of sufficient molecular weight to allow entanglement with the feather particles. For example, anionic polymers having a molecular weight of approximately 40,000 to 300,000 may be used. Preferably, the anionic polymeric adduct may be hydrolyzed polyacrylamide, hydrolyzed polyacrylonitrile, homopolymers or copolymers of acrylic acid, copolymers of acrylic acid and acrylamide, a combination of copolymers of acrylamide and anionic monomers, silica sols, or any combination of these or other anionic polymers known in the art. It should be appreciated that combinations of anionic polymeric adducts may also be used.

The anionic polymeric adduct is added in an amount sufficient to provide a uniform anionic charge distribution in the feathers, which may be determined by a colloid charge titration. Preferably, the anionic polymeric adduct is added to the slurry at a concentration of approximately 100–300 mg/kg of dry feather mass. The specific method of addition of the detergent to the wash solution may include a batch addition or a metered addition. The addition may also be continuous.

In the step 115, a cationic species is added to the slurry. Since the slurried feather mass possesses a significant anionic charge, to impart good dewatering properties and provide structural integrity, a cationic species is added. The cationic species may be any chemical compound having at least one cationic portion. Without being limited to any particular theory, it is believed that this cationic portion electrostatically bonds with the anionic polymeric adduct, which is meshed with or entangled with the feathers. The combination of the cationic species with the anionic polymeric adduct provides additional structural strength to the feather mass, which is useful in maintaining a cohesive feather mass as it is further processed.

The cationic species may be an inorganic species such as aluminum sulfate, aluminum chloride, aluminum chlorohydrate, aluminum silicate, phosphate, polyaluminum chloride, polyaluminum sulfate, polyaluminum sulfate silicate, ferrous or ferric iron, or an organic species such as cationic starch, homopolymers or copolymers of dimethyldiallyl ammonium chloride, epichlorihydrin alkylamine condensate polymers, and ethylene dichloride ammonia polymers. Preferably, the cationic species is a cationic polymer having a sufficient molecular weight to provide sufficient cohesiveness and structural integrity to the feather mass. Preferably, the cationic species is a higher molecular weight copolymer of acrylamide with a cationic monomer in excess of 1,000,000 molecular weight. More preferably, the cationic species is a polymer having a branched distribution, which may be obtained by polymerization with methylene bis-acrylamides or glyoxal crosslinking of the amide functions. It should be appreciated that combinations of various cationic species may also be used. For example, a copolymer or terpolymer of acrylamide in combination with a quaternary cationic monomer may be used. Additional cationic species that may be used are described in U.S. Pat. No. 6,238,486 to Dunham et al., which is incorporated herein by reference in its entirety.

The cationic species is added in an amount sufficient to provide acceptable dewatering properties for the feather mass. As will be discussed below, the feather mass is ultimately dewatered for use, and it is necessary to have a feather mass that allows sufficient dewatering. Further, the cationic species is added to provide structural integrity, specifically wet strength. After dewatering, the feather mass will still contain moisture but it is desirable to have a dewatered feather mass that has sufficient wet strength so that the feather mass remains intact as it is further processed. Therefore, the concentration of cationic species used may be determined based upon whether the feather mass exhibits acceptable dewatering properties and wet strength. Preferably, the cationic species is added to the slurry at a concentration of approximately 300–800 mg/kg of dry feather mass. The specific method of addition of the detergent to the wash solution may include a batch addition or a metered addition. The addition may also be continuous.

It should be appreciated that the addition of the anionic polymeric adduct and the cationic species may be performed sequentially, with either one being added before the other. In other words, the same benefits may be obtained by adding the anionic polymeric adduct before the cationic species, or visa versa. It should also be appreciated that various combinations of anionic polymer adducts and cationic species may also be used. For example, a copolymer or terpolymer of acrylamide with an anionic monomer may be used.

The addition of the cationic species also provides for the separation of at least a fraction of the quill portion of the feathers from the remainder of the feather mass. Specifically, the quill portion of the feather mass floats to the top of the slurried feathers after addition and mixing of the cationic species, while the remaining portion of the feather mass sinks. Therefore, this fraction of the quill portion may optionally be removed from the rest of the slurried feather mass if desired. Such removal may be performed by skimming the surface of the slurry or by selectively removing the upper portion of the slurry and filtering out the quill fraction.

At this point in the processing of the feathers, it should be appreciated that the slurry may be dewatered and the feather mass may be dried for subsequent use. For example, if the end use of the feather mass does not require a predetermined amount of structural integrity, then the feather mass may be acceptable as is. If, however, the end use of the feather mass is for incorporation into other products such that the feather mass will be providing some structural integrity to such products, then additional processing, as described below, may be desirable.

In the step 117, a structural additive is added to the slurried feathers. As noted, the feather mass may have sufficient structural integrity without the addition of a structural additive depending upon the desired end use of the feather mass. If the structural integrity or rigidity of the feather mass is not sufficient for the desired end use, such as for incorporation into the structure of other products, then the structural additive may be necessary. The addition of the structural additive may be accomplished by any means known in the art and may simply be mixed into the same tank and agitated in a manner similar to the addition of the anionic polymeric adduct and the cationic species. It should be appreciated that the structural additive may be added concurrently with either or both of the anionic polymeric adduct and the cationic species. Alternatively, the structural additive may be added after the addition of the anionic polymeric adduct and the cationic species.

The structural additive is added in an amount sufficient to provide the desired structural integrity. Preferably, the structural additive is added to the slurry at a concentration of approximately 2–5% by weight of dry feather mass and more preferably approximately 2–3% by weight of the dry feather mass. The specific method of addition of the detergent to the wash solution may include a batch addition or a metered addition. The addition may also be continuous.

The structural additive may be any chemical compound that imparts structural integrity or rigidity to the feather mass. Specifically, the structural additive may be a chemical compound that is water soluble and that adheres to the feathers in the feather mass during dewatering and that will thermoset and become water insoluble upon subsequent heating, such a drying of the feather mass. The structural additive may be a thermosetting polymer such as amine resins, amide resins, linear polyethylene, phenolics, alkyds, polyesters, and silicones.

Preferred polymers include amine resins, as they posses a degree of cationicity and are thus attracted into the feather mass. These amine resins may be substituted for the cationic polyacrylamides used as a cationic species; however, it is preferable to add the amine resins in addition to the cationic species. Typically, these amine resins are condensations of epichlorohydrin, alkylamine, and dicarboxylic acids, such as adipic acid, or condensations of methyl bis (aminopropyl) amine, epichlorohydrin, oxalic acid and urea. These amines resins are sold under the trade names KYMENE 557H and KYMENE 450 by the Hercules Corporation of Wilmington, Del. The inclusion of these polyamides in the range of 0.1 to 3% by weight of the dry feather mass provides desirable structural rigidity to a feather-based container or sheet when hot air dried.

In addition, crosslinking of polyacrylamides used as a cationic species, in particular, homopolymers and copolymers of polyacrylamides, with glyoxal has been found to also provide additional structural integrity or rigidity to the feather mass. As the glyoxal crosslinks the amide functions during drying of the feather mass discussed further below, the polymer crosslinks to a degree that water solubility is lost and significant structural integrity is gained.

In the step 119, the feather mass is dewatered. Dewatering made by accomplished using any means known in the art, such as by simple drainage of the liquid portion of the slurry or by filtering means, such as a vacuum filter belt, or centrifuge. It si preferable to dewater the feather mass to approximately 20–40% by weight of solids or feathers. The feather mass is then discharged from the dewatering equipment or the tank.

In the step 121, the feather mass from the dewatering equipment is then dried. Drying may be accomplished by any means known in the art, including, for example, air drying or through the use of heaters or ovens. It should be appreciated that the feather mass may be used for any other desired purpose before drying, including secondary processing. In this case, the wet strength of the feather mass after dewatering should be sufficient to allow further processing and handling of the feather mass without a significant loss of cohesiveness or integrity. After drying, however, the feather mass may be used in subsequent secondary processing for additional purposes or it may be rolled up as roll stock for subsequent secondary processing.

In the step 123, an anti-sloughing agent may be added to the dried feather mass. This agent is any chemical compound capable of reducing sloughing of minute feather matter or particulate matter from the feather mass. This agent may be applied by any means known in the art, such as spraying. Preferably, the anti-sloughing agent comprises polyvinyl alcohol, and, in particular, a 0.5% solution of polyvinyl alcohol. A chemical composition comprising polyvinyl chloride and a zirconium salt as a crosslinking agent may also be used. Other anti-sloughing agents include a polyvinyl acetate emulsion and a butadiene copolymer emulsion. It should be appreciated that the anti-sloughing agent may be used on the feather mass after any secondary processing of the feather mass as well.

The invention having been described, the following examples are presented to illustrate, rather than to limit the scope of the invention.

EXAMPLE 1

100 grams of chicken feathers obtained from a fresh slaughtering operation were hand chopped into manageable pieces and added to 10,000 grams of tap water. A standard laboratory mixer was used to agitate the feathers in the water. With agitation, 400 parts per million of a chemical composition consisting of the following, by weight, was added: 5.0% sodium metasilicate, 1.0% sodium EDTA, 10.0% sodium xylene sulfonate, 5.0% sodium octane sulfonate, 5.0% sodium laureth sulfate modified with 3 moles of ethylene oxide, 2.5% alkylaryl ether phosphate, and 71.5% water.

The feather slurry was agitated for 10 minutes, and the vessel was drained. The vessel was refilled with clean water and agitated for five minutes. The vessel was drained and the 100 grams of feathers recovered and air dried at 200F.

Testing performed on the feathers via hexane extraction showed no traces of fats or oils on the feathers, yet resistance to water was retained. Static charge testing showed significant anionic charge density on the feathers.

50 grams of the dried feathers were then slurried in 1500 grams of hot tap water. The slurry was then added to a standard laboratory blender, and the feathers were pulped to a uniform size. The contents of the blender were then added to a ball mill to achieve some fibrillation by crushing. The slurry was then poured into a standard handsheet former. Observed drainage, however, was poor. The resultant handsheet was easily removed from the former screen and dried. The finished handsheet showed good uniformity and distribution of feather mass. The dry strength of the product, however, was poor.

EXAMPLE 2

The procedure of Example 1 was repeated except that the following step was added: 50 mg/kg dry feathers of an anionic emulsion polymer was added to the slurry in dilute form. The polymer was a copolymer of acrylic acid and acrylamide in the mole ratio of 65% acrylic acid and 35% acrylamide. This was done in a vessel using a standard laboratory mixer. After 1.0 minute of mixing, a solution of 50 mg/kg of a cationic copolymer was added. The polymer was a copolymer of methacryloyl ethyl trimethyl ammonium chloride (METAC) and acrylamide in a ratio of 50 mole % METAC to 50 mole % acrylamide with a branched distribution.

A flocculation effect was immediately noticed as the cationic material bridged the feathers containing the anionic polymer. Quill particles were observed floating on the top of the vessel, and they were skimmed off. The slurry was again added to a standard handsheet former. Observed drainage was significantly better than that of Example 1. The sheet was easily removed from the screen and dried. The dried sheet was cohesive and significantly stronger than the sheet created in Example 1.

EXAMPLE 3

The procedure of Example 2 was repeated, except that after the addition of the cationic polymer, 2% by weight of a cationic thermosetting polyamide (HERCULES 557H) was added. The slurry was poured into a standard handsheet former. Observed drainage was again significantly better than that of Example 1. The sheet was easily removed from the screen and dried. The sheet was extremely rigid and showed good utility as a potential formed product.

EXAMPLE 4

The sheets generated in Examples 1, 2, and 3 showed some sloughing of minute feather particles when dried. To eliminate this, Examples 1, 2, and 3 were repeated, but prior to drying the handsheet, a 0.5% solution of polyvinyl alcohol was sprayed using a standard hand trigger sprayer on one side of each of the handsheets. This side was marked "A". The untreated side was marked "B". The handsheets were then dried. All three handsheets when dried showed no signs of sloughing or "dusting" on the "A" side. All three handsheets showed signs of sloughing on the "B" side, with Example 1 being the worst.

While the foregoing description and drawing represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. The presently disclosed embodiments are therefore to be considered in all respects as illustrative and not restrictive, the scope of the invention being indicated by the appended claims, and not limited to the foregoing description.

For example, it is to be understood that although the invention has been described using separate steps, many of the steps may be performed concurrently. Further, each of the specific chemical additives, including the anionic polymeric adduct, the cationic species, and the structural additive may be either a single chemical compound or a chemical composition comprising a mixture of different chemical compounds. Also, as noted above, many of these chemical compounds or mixtures may be added together or separately.

What is claimed is:

1. A method for processing poultry feathers, comprising:
    contacting a plurality of poultry feathers having an average particle size with a detergent capable of imparting a static charge to said plurality of poultry feathers;
    reducing said average particle size of said plurality of poultry feathers;
    increasing entanglement of said plurality of poultry feathers;
    adding an anionic polymeric adduct to said plurality of poultry feathers;
    adding a cationic species to said plurality of poultry feathers; and
    dewatering said plurality of poultry feathers.

2. The method of claim 1, wherein said plurality of poultry feathers comprise fats and oils and wherein said detergent comprises a chemical compound capable of removing at least a portion of said fats and oils from said plurality of poultry feathers.

3. The method of claim 1, wherein said detergent comprises a chemical compound selected from the group consisting of: alkyl amine oxides, ethylene oxide adducts of alcohols, propylene oxide adducts of alcohols, phosphate esters, ethylene oxide/propylene oxide block copolymers, alkyl ethers, alkyl ether sulfates, alkoxylated alkyphenols, fatty betaines, fatty amine betaines, ethylene oxide adducts of fatty acids, propylene oxide adducts of fatty acids, glycosides, alkyl benzene sulfonic acids, alkyl benzene sulfonates, olefin sulfonates, neutralized fatty acid amides, alcohol sulfates, neutralized salts of alcohol sulfates, fatty acid alkanolamides, polyethylene glycol esters of fatty carboxylic acids, glycol ethers, butyl solvents, sodium silicate, metasilicates, phosphates, alkanolamines, and combinations thereof.

4. The method of claim 1, where said detergent comprises a mixture of a glycol ether and a chemical compound selected from the group consisting of: alkyl amine oxides, ethylene oxide adducts of alcohols, propylene oxide adducts of alcohols, phosphate esters, ethylene oxide/propylene oxide block copolymers, alkyl ethers, alkyl ether sulfates, alkoxylated alkyphenols, fatty betaines, fatty amine betaines, ethylene oxide adducts of fatty acids, propylene oxide adducts of fatty acids, glycosides, alkyl benzene sulfonic acids, alkyl benzene sulfonates, olefin sulfonates, neutralized fatty acid amides, alcohol sulfates, neutralized salts of alcohol sulfates, fatty acid alkanolamides, polyethylene glycol esters of fatty carboxylic acids, butyl solvents, sodium silicate, metasilicates, phosphates, alkanolamines, copolymers of acrylamide, terpolymers of acrylamide, an ammonium salt of an acrylate homopolymer, an ammonium salt of an acrylate copolymer, an ammonium salt of an acrylate terpolymer, an sodium salt of an acrylate homopolymer, an sodium salt of an acrylate copolymer, an sodium salt of an acrylate terpolymer, a fully hydrolyzed acrylamide homopolymer, a partially hydrolyzed acrylamide homopolymer, and combinations thereof.

5. The method of claim 4, further comprising a butyl solvent.

6. The method of claim 1, where said detergent comprises a mixture of a dispersing aid and a chemical compound selected from the group consisting of: alkyl amine oxides, ethylene oxide adducts of alcohols, propylene oxide adducts of alcohols, phosphate esters, ethylene oxide/propylene oxide block copolymers, alkyl ethers, alkyl ether sulfates, alkoxylated alkyphenols, fatty betaines, fatty amine betaines, ethylene oxide adducts of fatty acids, propylene oxide adducts of fatty acids, glycosides, alkyl benzene sulfonic acids, alkyl benzene sulfonates, olefin sulfonates, neutralized fatty acid amides, alcohol sulfates, neutralized salts of alcohol sulfates, fatty acid alkanolamides, polyethylene glycol esters of fatty carboxylic acids, butyl solvents, sodium silicate, metasilicates, phosphates, alkanolamines, and combinations thereof.

7. The method of claim 6, wherein said dispersing aid comprises a chemical compound selected from the group consisting of: a homopolymer of acrylic acid, a copolymer of acrylic acid, and a terpolymer of acrylic acid.

8. The method of claim 1, wherein said reducing said average particle size of said plurality of poultry feathers and said increasing entanglement of said plurality of poultry feathers are performed concurrently.

9. The method of claim 8, wherein said reducing said average particle size comprises passing said plurality of feathers through a mill.

10. The method of claim 8, wherein said reducing said average particle size comprises reducing a standard deviation associated with said average particle size.

11. The method of claim 1, wherein said increasing said entanglement of said plurality of poultry feathers comprises increasing fibrillation of a plurality of keratin strands associated with said plurality of poultry feathers.

12. The method of claim 1, wherein said anionic polymeric adduct comprises a chemical compound capable of increasing entanglement of said plurality of poultry feathers.

13. The method of claim 1, wherein said anionic polymeric adduct comprises an anionic polymer.

14. The method of claim 12, wherein said anionic polymeric adduct comprises a chemical compound selected from the group consisting of: hydrolyzed polyacrylamide, hydrolyzed polyacrylonitrile, homopolymers of acrylic acid, copolymers of acrylic acid and acrylamide, copolymers acrylamide and anionic monomers, silica sols, and combinations thereof.

15. The method of claim 1, wherein said cationic species comprises a chemical compound capable of increasing dewatering properties of said plurality of poultry feathers and binding to said anionic polymeric adduct.

16. The method of claim 1, wherein said cationic species comprises an inorganic chemical compound selected from the group consisting of: aluminum sulfate, aluminum chloride, aluminum chlorohydrate, aluminum silicate, phosphate, polyaluminum chloride, polyaluminum sulfate, polyaluminum sulfate silicate, ferrous iron, ferric iron, and combinations thereof.

17. The method of claim 1, wherein said cationic species comprises an organic chemical compound selected from the group consisting of: cationic starch, homopolymers of dimethyldiallyl ammonium chloride, copolymers of dimethyldiallyl ammonium chloride, epichlorihydrin alkylamine condensate polymers, ethylene dichloride ammonia polymers, and combinations thereof.

18. The method of claim 1, wherein said cationic species comprises copolymers of acrylamide and a cationic monomer having a molecular weight greater than approximately 1,000,000.

19. The method of claim 1, wherein said cationic species comprises a chemical compound selected from the group consisting of: a branched polymer produced from polymerization using methylene bis-acrylamides and a branched polymer produced from glyoxal crosslinking of amide functional groups.

20. The method of claim 1, further comprising rinsing said plurality of feathers after said contacting with said detergent and before said reducing of said average particle size.

21. The method of claim 1, further comprising adding an antimicrobial compound to said plurality of poultry feathers.

22. The method of claim 1, further comprising separating a plurality of quills from said plurality of poultry feathers after said adding said cationic species to said plurality of poultry feathers.

23. The method of claim 1, further comprising adding a structural additive to said plurality of poultry feathers before said dewatering of said plurality of poultry feathers.

24. The method of claim 23, wherein said structural additive comprises a thermosetting polymer selected from the group consisting of: amine resins, amide resins, linear polyethylene, phenolics, alkyds, polyesters, silicones, and combinations thereof.

25. The method of claim 23, wherein said amine resins are selected from the group consisting of: condensations of epichlorohydrin, alkylamine, and dicarboxylic acids and condensations of methyl bis (aminopropyl) amine, epichlorohydrin, oxalic acid and urea.

26. The method of claim 1, wherein said cationic species comprises a cationic polyacrylamide copolymer and glyoxal.

27. The method of claim 1, further comprising adding a polyvinyl alcohol to said plurality of poultry feathers.

* * * * *